US010244675B2

(12) United States Patent
LaRowe (10) Patent No.: US 10,244,675 B2
(45) Date of Patent: Apr. 2, 2019

(54) FIELD ROBOT

(71) Applicant: Veritas FC LLC, Spokane, WA (US)

(72) Inventor: Gavin LaRowe, Spokane, WA (US)

(73) Assignee: Veritas FC LLC, Spokane, WA (US)

( * ) Notice: Subject to any disclaimer, the term of this patent is extended or adjusted under 35 U.S.C. 154(b) by 0 days.

(21) Appl. No.: 15/418,282

(22) Filed: Jan. 27, 2017

(65) Prior Publication Data

US 2018/0020611 A1 Jan. 25, 2018

Related U.S. Application Data (60) Provisional application No. 62/289,176, filed on Jan. 29, 2016.

(51) Int. Cl.
*A01C 21/00* (2006.01)
*H02S 50/00* (2014.01)
(Continued)

(52) U.S. Cl.
CPC ............ *A01C 21/007* (2013.01); *A01B 51/02* (2013.01); *A01B 69/008* (2013.01); *A01B 79/005* (2013.01); *A01C 21/005* (2013.01); *A01C 23/006* (2013.01); *A01C 23/042* (2013.01); *A01G 7/045* (2013.01); *A01G 9/26* (2013.01);
(Continued)

(58) Field of Classification Search
CPC ... A01C 21/007; A01C 21/005; A01C 23/006; A01C 23/042; A01B 51/02; A01B 69/008; A01B 79/005; A01G 7/045; A01G 9/26; A01G 13/0206; A01G 25/09; A01G 25/167; A01M 25/006; A01M 31/002; G05D 1/0022; G05D 1/0088; G05D 1/0225; G05D 1/0287; G05D 2201/0201; G07C 5/008; H02S 20/30; H02S 30/20; H04W 4/80; H04W 84/18; B60Q 1/02; G01N 33/24; G01S 19/13; G05B 2219/45017; Y10S 901/01
See application file for complete search history.

(56) References Cited

U.S. PATENT DOCUMENTS

2008/0148631 A1* 6/2008 Wan .................. A01G 13/0206
47/22.1
2015/0105965 A1* 4/2015 Blackwell ............ A01B 59/002
701/28

(Continued)

FOREIGN PATENT DOCUMENTS

WO WO-2013181069 A1 * 12/2013 ........... A01C 21/002

*Primary Examiner* — Lail A Kleinman
*Assistant Examiner* — Mahmoud M Kazimi
(74) *Attorney, Agent, or Firm* — Han Santos, PLLC; Elliott Y. Chen (57) ABSTRACT

Autonomous mobile field robots may be used to maintain fields. An autonomous mobile field robot may perform soil mechanics with environment sensors at a sub-region and store the soil mechanics. The robot may further determine soil temperature of the sub-region and store the soil temperature. The soil mechanics and the soil temperature are sent to a monitoring server via a radio access network for storage and analysis. The parameters for the soil of the sub-region may be adjusted based on the soil mechanics of the sub-region with the chemicals from chemical storage units. The robot may return to a home station to refill one or more of the water or chemicals.

20 Claims, 5 Drawing Sheets

(51) Int. Cl.

| | | |
|---|---|---|
| *G05D 1/02* | (2006.01) |
| *A01B 79/00* | (2006.01) |
| *A01B 51/02* | (2006.01) |
| *A01G 9/26* | (2006.01) |
| *A01G 25/09* | (2006.01) |
| *A01G 13/02* | (2006.01) |
| *A01M 31/00* | (2006.01) |
| *G05D 1/00* | (2006.01) |
| *A01M 25/00* | (2006.01) |
| *A01C 23/04* | (2006.01) |
| *A01G 25/16* | (2006.01) |
| *G07C 5/00* | (2006.01) |
| *A01G 7/04* | (2006.01) |
| *A01B 69/04* | (2006.01) |
| *A01C 23/00* | (2006.01) |
| *H04W 4/80* | (2018.01) |
| *G01S 19/13* | (2010.01) |
| *H02S 30/20* | (2014.01) |
| *H04W 84/18* | (2009.01) |
| *H02S 20/30* | (2014.01) |
| *G01N 33/24* | (2006.01) |
| *B60Q 1/02* | (2006.01) |

(52) U.S. Cl.
CPC ......... *A01G 13/0206* (2013.01); *A01G 25/09* (2013.01); *A01G 25/167* (2013.01); *A01M 25/006* (2013.01); *A01M 31/002* (2013.01); *G05D 1/0022* (2013.01); *G05D 1/0088* (2013.01); *G05D 1/0225* (2013.01); *G05D 1/0278* (2013.01); *G05D 1/0287* (2013.01); *G07C 5/008* (2013.01); *H02S 50/00* (2013.01); *B60Q 1/02* (2013.01); *G01N 33/24* (2013.01); *G01S 19/13* (2013.01); *G05B 2219/45017* (2013.01); *G05D 2201/0201* (2013.01); *H02S 20/30* (2014.12); *H02S 30/20* (2014.12); *H04W 4/80* (2018.02); *H04W 84/18* (2013.01); *Y10S 901/01* (2013.01)

(56) References Cited

U.S. PATENT DOCUMENTS

| | | | |
|---|---|---|---|
| 2016/0073591 A1* | 3/2016 | Surany | F24S 90/00 47/32.3 |
| 2016/0157414 A1* | 6/2016 | Ackerman | A01B 69/008 701/25 |
| 2016/0195876 A1* | 7/2016 | Mattsson | A01G 25/16 701/25 |
| 2017/0020087 A1* | 1/2017 | Younis | A01G 25/16 |
| 2017/0126172 A1* | 5/2017 | Nogier | A01G 9/243 |

* cited by examiner

FIELD ROBOT

CROSS REFERENCE TO RELATED PATENT APPLICATION

This application claims priority to U.S. Provisional Patent Application No. 62/289,176, filed on Jan. 29, 2016, entitled "Field Robot," which is hereby incorporated by reference in its entirety.

BACKGROUND

Field activities, such as planting, tending, mowing, and harvesting use a range of tools, equipment, and machinery that require skilled operators. In recent years, advances in technology have substantially reduced the work load of the field operators. Modern farmers and field operators may have global positioning systems (GPS) and as well as and auto-steer systems to guide their tractors through the field. Further, field operators may use field management software and GPS receivers to map their fields and to determine the general condition of their field. Separately, a farmer may perform soil measurements to determine the health of their soil. Based on their collected and mapped data, a farmer, can generate prescription maps that specify how much water or fertilizer to apply to the field, how densely to plant the seeds, and the like. The farmer may also determine the weather forecast and adjust the fixed sprinkler system for when and how long the field should be irrigated.

Thus, while field maintenance has significantly modernized, it relies on disparate technologies that have not been synthesized to work in concert to provide autonomous administration of the field that is independent of fixed irrigation systems, predetermined schedules, and/or fixed routes. There is no present system and method that can autonomously provide irrigation, shading, feeding, refilling, artificial lighting, and remote health analysis of a field.

BRIEF DESCRIPTION OF THE DRAWINGS

The detailed description is described with reference to the accompanying figures, in which the left-most digit(s) of a reference number identifies the figure in which the reference number first appears. The use of the same reference numbers in different figures indicates similar or identical items.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

This disclosure generally relates to maintaining a field, and more particularly, to autonomous mobile field robots that are configured to be used on a field. The field robot is configured to autonomously determine the parameters of the sub-regions of a field and provide an administration of the field with a custom solution for each sub-region of the field. In various embodiments, the field robot is configured to determine a map of the field, identify a path, and for each sub-region of the field: perform soil mechanics, determine soil temperature, and communicate the determined soil metrics to a monitoring server.

In addition to providing remote health analysis, for each sub-region of the field, the field robot can autonomously provide irrigation, adjust one or more soil parameters, provide shade, and artificial lighting to mimic the ultra-violet rays of natural light (i.e., sun) to promote the health of each sub-region of the field. Instead of being driven by a rigid predetermined schedule, the field robot calculates an intelligent schedule and path based on information from various sensors and machine learning to provide a tailored administration of each sub-region of the field. In various embodiments, the field robot may work independent of or in concert with other field robots by wirelessly communicating relevant information to a monitoring server and/or other field robots. Thus, the functions discussed herein that are performed by a robot may be performed by (i) a single robot, (ii) a plurality of similar robots that work in concert, each having similar capabilities, (iii) and a plurality of robots that intelligently divide their labor, each robot being more specialized to perform their particular task.

Accordingly, in various embodiments, the field robot provides self-learning behaviors based on the soil metrics of the sub-regions of a field. The soil metrics may be analyzed by the field robot itself, by a remote monitoring server, or a combination thereof. Additional information relevant to the field, such as weather forecast and historic information of this field (or other similar fields) from a remote server, such as a monitoring server and/or other data store, may be retrieved for machine learning. The techniques described herein may be implemented in a number of ways. Example implementations are provided below with reference to the following figures.

Example Architecture

Figure 1:
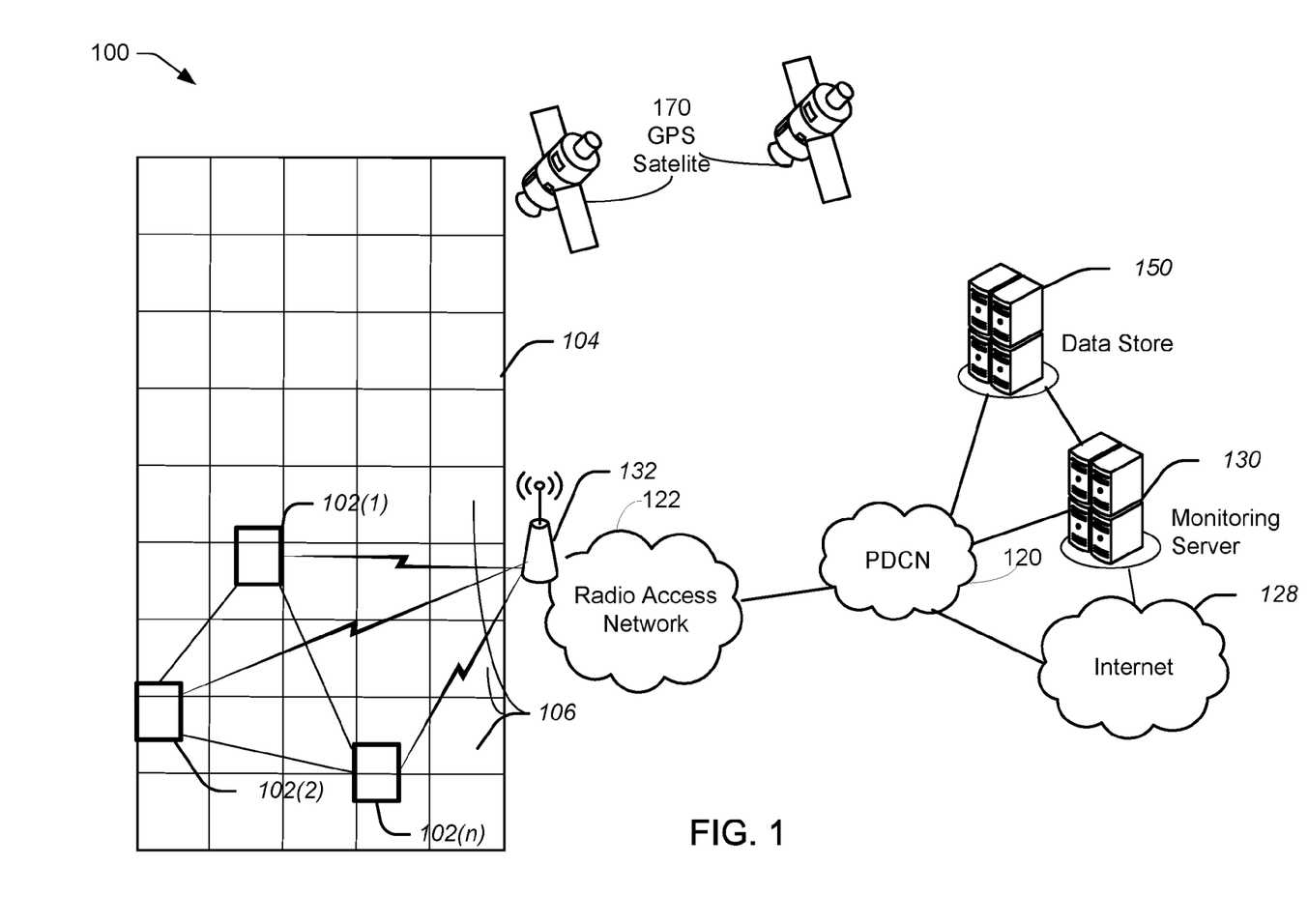
FIG. 1 illustrates an example architecture for implementing an autonomous mobile field robot system.

FIG. 1 illustrates an example architecture for implementing an autonomous mobile field robot system. FIG. 1 illustrates an architecture comprising a field 104 that includes many sub-regions 106. In various embodiments, there may be a single field robot (FR) or a plurality of FRs that work in concert to administer the field 104. Each FR may be identical or specialized to perform their function. There is a radio access network (RAN) that may be part of the mobile communication network, which provides communications between FR's 102(1) to 102(n), as well as communication with networks and/or stations that are outside the RAN 122, like a monitoring server 130 and/or a data store 150. Thus, the RAN allows the FR's to communicate via a packet data communication network (PDCN) 120.

Figure 2:
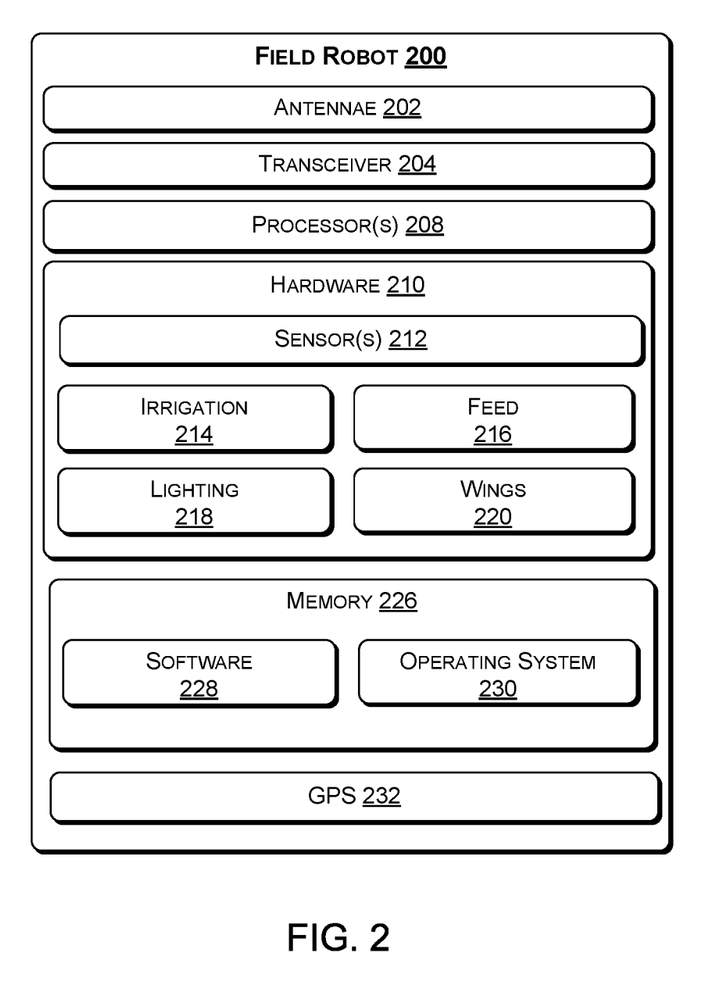
FIG. 2 illustrates a block diagram of an exemplary field robot that may be used in the architecture of FIG. 1.
Figure 3A:
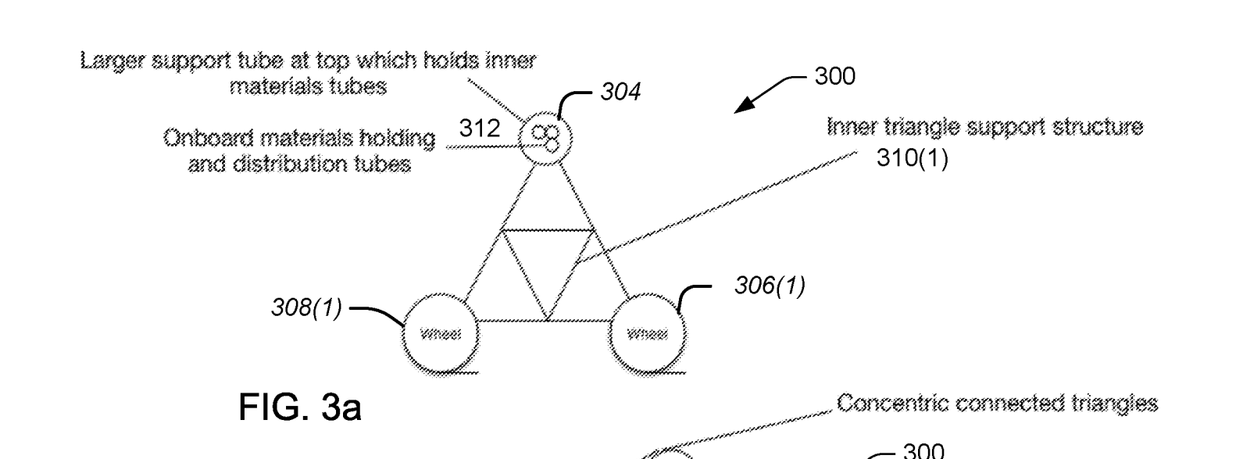
FIG. 3a illustrates a simplified side view of an example field robot.
Figure 3B:
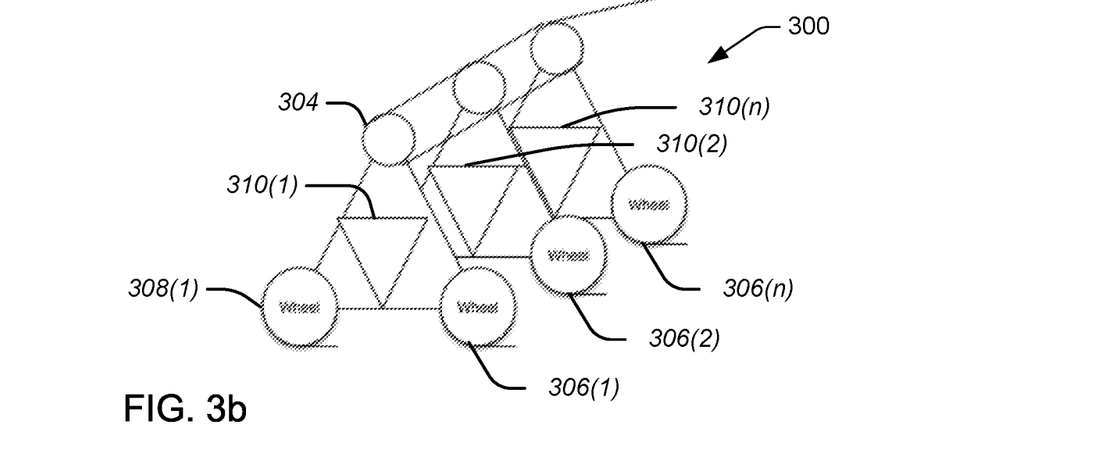
FIG. 3b illustrates a perspective view of an example field robot.

For purposes of later discussion, several FR's appear in the drawing, while it will be understood based on the discussion herein that the functions can be performed by a single FR. The actual configuration of an FR is discussed in more detail later in the context of FIGS. 2 and 3.

Each FR (e.g., 102(1) to 102(n)) may include a Global Positioning System (GPS) receiver that receives and processes signals from GPS satellites 170 to determine its geographic location. GPS 170 provides accurate position information in locations where the FR can receive the signals from the GPS satellites. In one embodiment, the space-based satellite navigation system of GLONASS is used to add more satellites, and thereby more quickly and accurately establish the location of the FR. Accordingly, high-precision augmented GPS may be used to provide navigation precision that is accurate to a few inches, thereby further facilitating the precise administration of each sub-region 106 of the field 104. Thus, an FR (e.g., 102(1)) can record its route and it (or another FR) can reproduce the route at a later time.

For example, if an FR senses an obstacle, such as a ditch, tree, boulder, etc., it may use its artificial intelligence to navigate around it. Its learned route may be stored and used by the same or another FR at a more efficient pace (without having to slow down to learn about obstacles).

In one embodiment, images from satellites, similar to those of GPS 170, may be used to provide each FR a detailed map of the field 104. The GPS receiver of an FR can be used together with the map to navigate through the field 104 with the aid of the GPS 170.

Physical elements of a RAN 122, operated by one of the mobile service providers or carriers, include a number of base stations, represented in the example of FIG. 1 by a base station 132. Such base station 132 may include a base transceiver system (BTS) that communicates via an antennae system at the site of the node and over the air-link with one or more of the FR's (102(1) to 102(n)). While a single base station 132 is illustrated, it will be understood that RAN 122 may have multiple base stations 132. Each base station 132 node may include a BTS coupled to several antennae mounted on a base station within a coverage area often referred to as a "cell." The BTS is the part of the radio network that sends and receives RF signals to/from the FR's that the base station 132 currently serves.

The radio access network 122 carries the user communications for the FR's between base station 132 and other elements with or through which the FR's communicate. Individual elements such as switches and/or routers forming the radio access network 122 are omitted here for simplicity. It will be understood that the various network elements can communicate with each other, as well as other aspects of the RAN 122 and the Internet 128 either directly or indirectly. System 100 includes one or more private IP type packet data networks 120 based on a packet data communication network (PDCN), sometimes referred to as an Intranet, (i.e., a private network).

Communication via the private network 120 may provide additional services, such as remote health monitoring the field via a monitoring server 130 and a data store 150, which may be coupled for communication via the private network 120.

In the example of FIG. 1, there is a remote monitoring server 130 that is configured to receive soil metrics of the sub-regions 106 of the field 104, as well as other information, from one or more FR's. In one embodiment, the monitoring server 130 receives the information from the respective in the form of a data package over the RAN 122 and PCDN 120. In various embodiments, the data package may include identification (ID) information of the respective FR, soil metrics, and other metrics related to each sub-region of the field 104.

In one embodiment, system 100 includes a data store 150 where the soil metrics of each sub-region are stored for subsequent processing and analysis. In various embodiments, the data store 150 may include historic information, including soil metrics and other soil health metrics provided by the one or more FR's 102(1) to 102(n).

In one embodiment, the monitoring server 130 together with the data store 150 perform machine learning to construct algorithms that can learn from and make predictions based on the data stored in the data store 150. Such algorithms operate by building a model from stored prior inputs or baselines therefrom in order to make data-driven predictions or decisions. In one embodiment, these algorithms are used to provide threshold conditions that may be used to provide a soil care by one or more FR's. Accordingly, care is tailored for each sub-region, rather than following strictly static criteria.

For example, based on the machine learning, patterns and trends are identified (e.g., from the determined soil metrics and other metrics). Any outliers from the identified patterns and trends are identified as requiring special care, such as a calculated amount of irrigation, more or less radiation (e.g., via shade or artificial lighting), and/or a tailored adjustment of the parameters of the soil via chemicals.

In various embodiments, the machine learning discussed herein may be supervised or unsupervised. In supervised learning, the monitoring server 130 may be presented with example data from the data store 150 as being acceptable. Put differently, the data store 150 acts as a teacher for the monitoring server 130. In unsupervised learning, the data store 150 does not provide any labels as what is acceptable, rather, it simply provides historic data to the monitoring server 130 that can be used together with the recently determined data (e.g., sol metrics) from the one or more FR's to find its own structure among the data.

In some embodiments, the FR's 102(1) to 102(n), instead of or in addition to using RAN 122, the FR's 102(1) to 102(n) communicate with each other through one or more short range wireless transceivers while keeping off its cellular transceiver (e.g., to conserve power and/or cost of operation). The various wireless technologies that may be used by the FR include (but are not limited) to Digital Enhanced Cordless Telecommunications (DECT), Near Field Communication (NFC), ZigBee, and Bluetooth. DECT technology (traditionally used for wireless home phone systems) uses substantially less energy than cellular systems. NFC is a set of standards for smart-phones and similar devices to establish radio communication with each other by touching them together or bringing them into close proximity, usually no more than a few centimeters. Since the range is small, there are substantial power consumption benefits. In such an embodiment, each FR is in very close (e.g., <20 cm) proximity during data exchange.

Bluetooth, while operating at longer distances than NFC, still saves a substantial amount of power compared to cellular systems. ZigBee is a low-cost, low-power, wireless mesh network standard. The mesh networking of ZigBee provides high reliability and more extensive range (e.g., 50 m).

While the monitoring server 130 and the data store 150 are illustrated by way of example as separate servers, they may be implemented on different hardware platform combinations. Thus, the functionality described herein with respect to each of the servers 130 and 150 can also be provided by one or multiple different computing devices. In other words, the monitoring server 130 and data store 150 need not be a stand-alone computing devices but can be combined in various configurations.

Example User Device Components

With the foregoing overview of the system, it may be helpful now to consider a high-level discussion of an example FR. For purposes of such a discussion, FIGS. 2 and 3a/3b provide a block diagram and a simplified structural diagram, respectively, of an exemplary FR 200. The FR 200 may include one or more antennae 202, transceiver 204, user interface 206, one or more processors 208, hardware 210, and memory 226.

In some embodiments, the antennae 202 include an uplink antenna that sends radio signals to a base station (e.g., 132 in FIG. 1), and a downlink antenna that receives radio signals from the base station. In other embodiments, a single antenna may both send and receive radio signals. These signals may be processed by a transceiver 204 that is configured to receive and transmit data.

The FR 200 may include one or more processors 208, which may be a single-core processor, a multi-core processor, a complex instruction set computing (CISC) processor, or another type of processor. The hardware 210 may include a power source and digital signal processors (DSPs), which may include single-core or multiple-core processors. The processors may perform operation in parallel to process a stream of data that may be provided by probe application and/or operating system 230.

The hardware 210 may also include network processors that manage high speed communication interfaces, including communication interfaces that interact with peripheral components. The network processors and the peripheral components may be linked by switching fabric. The hardware 210 may further include hardware decoders and encoders, a network interface controller, and/or a universal serial bus (USB) controller.

The network interface controller may enable the processors to transmit and receive data via the radio access network of FIG. 1. In some embodiments, the hardware 210 may also include a direct memory access (DMA) engine. The DMA engine may enable the various controllers to access the memory 226 independently of the one or more processors 208 to perform tasks. The various controllers and processors of the FR 200 may execute instructions and perform tasks under the direction of software components that are stored in the memory 226.

The hardware 210 of the FR 200 may include one or more sensors 212, sometimes referred to herein as environment sensors. The environment sensors may include, but are not limited to, a temperature sensor, a humidity sensor, an imaging device, a nutrient sensor, a chemical composition sensor, an acidity sensor, a pH sensor, a contaminant level sensor, a water content sensor, a specific gravity sensor, a liquid limit sensor, and a plastic limit sensor.

The hardware 210 may further include a water storage device (e.g., container pipe) for irrigation 214 and one or more storage devices for feed 216, such as various chemicals for adjusting one or more parameters of the soil of a sub-region.

There may be one or more collapsible set of wings 220 for shade. In one embodiment, each wing 220 has a first side that includes a solar panel configured to gather charge. The wing may be opened up with the first side facing the sun to provide shade to a sub-region or a portion thereof. In various embodiments, the wings may be fixed to the FR 200 or can be deployed (e.g., like mobile umbrellas) to sub-regions that have been deemed by an FR 200 to benefit from shade. In the case of detachable wings that can be deployed, the FR 200 stores the exact location of the deployed wings and later picks up (or instructs another FR 200 to pick up) the deployed wings, when a calculated threshold time has elapsed or when the wings are no longer beneficial (e.g., the natural light is no longer shining on the subject sub-region). In one embodiment, each wing includes a battery that stores charge, which can later be transferred to the FR 200 upon pickup.

In one embodiment, FR 200 includes artificial lighting that mimics the spectrum of the sun. In various embodiments, the artificial lighting may be fixed to the FR 200 or deployed, similar to the wings discussed above. Thus, upon the FR 200 determining, based on the soil metrics that a sub-region (or a portion thereof) would benefit from additional (e.g., UV) lighting, then the artificial light can be turned on.

The data determined by the sensor(s) 212, collectively referred to herein as soil metrics, may be sent by the transceiver 204 of an FR 200 to the monitoring server 130 and/or other monitoring servers.

The memory 226 may be implemented using computer-readable media, such as computer storage media. Storage media includes volatile and non-volatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD), high definition video storage disks, or other optical storage, magnetic cassettes, magnetic tape, magnetic disk storage or other magnetic storage devices, or any other non-transmission medium that can be used to store information for access by a computing device.

The memory 226 may store various software components that are executable or accessible by the processors 208 and controllers of the FR 200. The various components may include software 228 and an operating system 230. Each module may include routines, program instructions, objects, and/or data structures that perform particular tasks or implement particular abstract data types.

The software 228 may enable the FR 200 to perform functions and control hardware components, including the sensors 212, of the FR 200. In various embodiments, the software 228 may provide various functions, such as determining the appropriate route to take in the field 104, the type of soil metrics to perform, what chemicals to apply, whether and how long to provide shade, whether and how long to provide artificial lighting, when to return to the home station, etc.

In one embodiment, FR 200 includes a GPS receiver 232 and an associated antenna. As discussed above, GPS is a space-based satellite navigation system that provides location and time information anywhere on Earth, where there is an unobstructed line of sight to at least three, four, or more of the GPS satellites. In various embodiments, the GPS receiver 232 may measure the latitude and longitude, direction of travel, speed of travel, elevation at all wheels or points of contact with the ground, slope gradient, elevation, etc.

Under control of the processor(s) 208, the GPS receiver 232 receives and processes signals from one or more satellites of the constellation of GPS satellites. From its processing, the GPS receiver 232 supplies GPS data to the processor 208. In some configurations, the GPS receiver determines the actual position fix and supplies data such as latitude and longitude to the microprocessor of the FR. In other implementations, the GPS receiver 232 takes pseudo-range measurements from received satellite signals and supplies the measurements to the processor 208 for use in determining the position fix. Hence, associated computations to make an actual location determination may be performed in the processor 208 or by a processor or the like included in the GPS receiver 232.

In this way, the GPS receiver 232 receives and processes signals from three or more of the GPS satellites to enable the processor(s) 208 to determine the location of the FR 200 in real time as the robot travels about. The device may implement location determination in a standalone mode or a network assisted mode. Standalone GPS operation uses radio signals from satellites alone. On the other hand, Assisted GPS (A-GPS) additionally uses network resources to 'assist' in the determination of device location, for example, in poor satellite signal conditions. The GPS receiver alone, or in combination (aGPS) with other network elements can enable the FR 200 to determine the latitude and longitude, which the FR 200 or a server in communication with the FR 200 can use in a variety of ways, e.g., to map current location and/or provide navigation directions to another location.

The operating system 230 may include components that enable the FR 200 to receive and transmit data via various interfaces (e.g., user interface 206, communication interfaces, etc.). The operating system 230 may also receive instructions from the probe application, harvest at least some of the soil metrics of the processes running during and/or at predetermined time periods using the one or more processors 208, based on the instructions received from the probe application. For example, the operating system 230 may provide an execution environment for the execution of the software 228 and other software applications. Additionally, the operating system 230 may include other components that perform various other functions generally associated with an operating system.

FIG. 3*a* illustrates a simplified side view of an example FR 300 and FIG. 3*b* illustrates a perspective view of an example FR 300. In various embodiments, the FR 300 may comprise steel alloy, carbon fiber, or graphene. The vertical shape may be triangular 310(1) with two wheels 306(1) and 308(1) at the bottom of the triangular frame 310(1) for each connected triangular shape (310(1) to **310(*n*)**) of the frame.

In one embodiment, the frame is tubular and comprises a series of triangular shapes (310(1) to **310(*n*)) attached via the top tube 304 and support arms that connect the concentric triangular shapes and may include two rectangular wings that will be secured to the top tube of a given triangular shape. Alternatively, the wings can be detached for deployment to a sub-region of a field. These wings can be set in the vertical position to let light through or in the horizontal position to block light from coming through. The top of the wings may comprise solar panels that may charge the FR 300 either directly or a battery attached to the wing, wherein the battery then later charges the FR 300** upon extraction. In one example, the wings may be at a flat 90/300 angle and collecting solar power via the panels on top of the wings. When not providing shade, the wings may be vertical and while collecting fractional solar power, depending on the orientation of the solar panel and location/direction of the sun.

In one embodiment, the bottom of the wings include (e.g., UV emitting) lights that are powered by the energy harvested from the solar panels in the wings. In another embodiment, the energy to power the light is provided by one or more batteries that were previously stored via an electrical connection (e.g., socket) to an outlet. These lights may be turned on at night to increase growing time for the crops/grass in question. In one embodiment these batteries may also be used to power various other aspects of the robot, such as its wings.

In one embodiment, the top tube 304 acts as an axle and comprises three or more internal tubes 312 within this vertical stabilizing tube that is part of the top of the triangular shapes 310(1). In various embodiments the chemical storage units (e.g., tubes) may comprise water, fertilizer, feed, pesticide, etc. The tubes themselves may have various fixtures/mechanisms/motors and plumbing for distributing the materials in the internal tubes. In various embodiments, there is an area in the middle or on the ends of the tube 304 to house the computers/computing and telecommunications fixtures/equipment for the FR 300.

In one embodiment, the triangularly-shaped support structures on the periphery (e.g., 306(1) and **306(*n*)) may include various automated hoses/arms that may allow the FR 300 to automatically couple with supply fixtures at a home station during docking, for various materials (e.g., water, fertilizer, feed, pesticide, etc.) to replenish the chemical storage units and water (e.g., internal tubes 312). In one embodiment, the battery is recharged as well. The FR 300 may report supply levels to the monitoring server 130. In one embodiment, FR 300 includes solid material wheels 308(1) and 306(1) to 306(*n*) on the bottom triangularly-shaped support structures 310(1) to 310(*n*). Advantageously, since the structure of the FR 300** is not bound by a center or side pivot as known agricultural watering systems, the irrigation and the dispensing of the chemicals can be administered at any sub-region of the field.

Example Process

Figure 4:
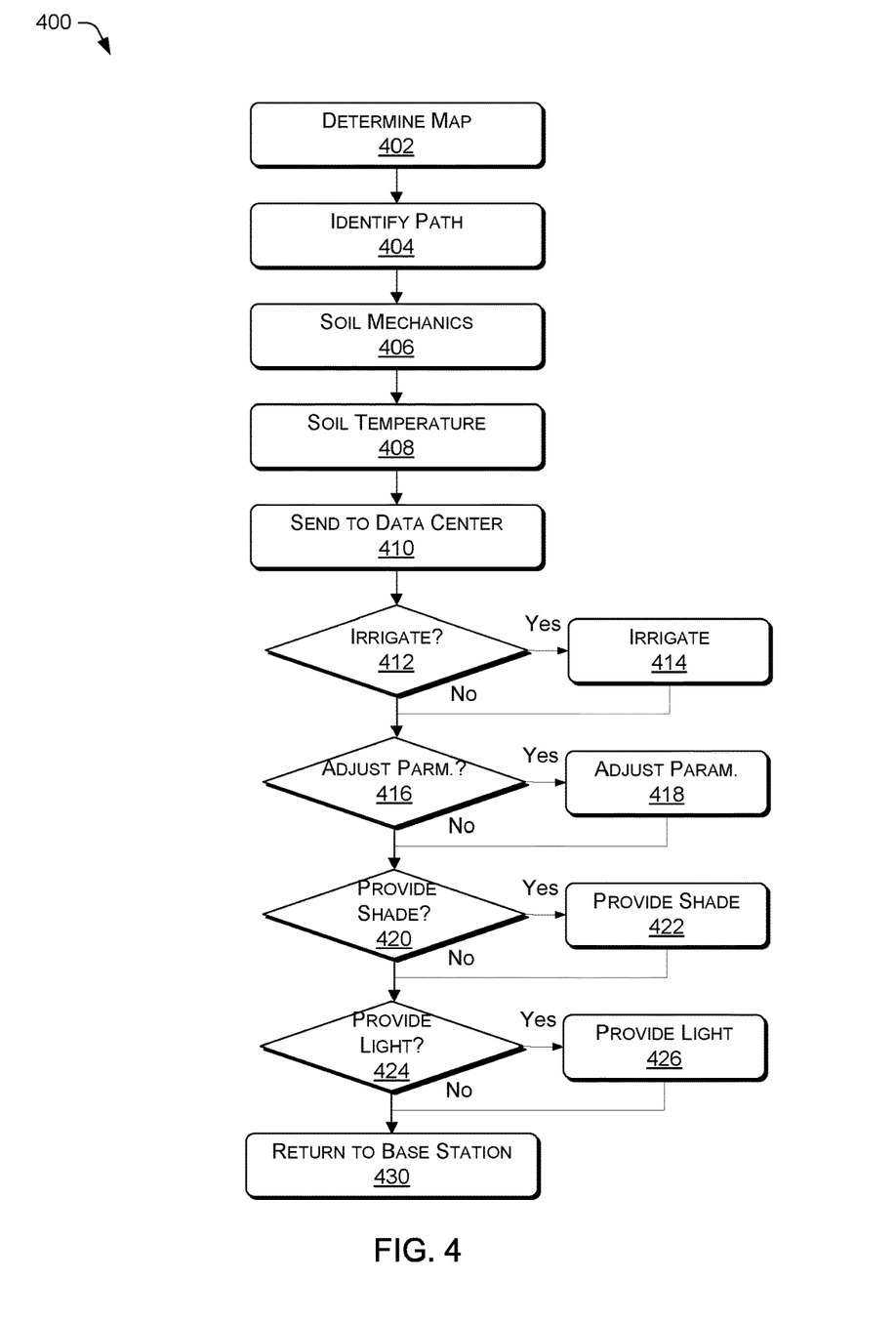
FIG. 4 is an illustrative process for an autonomous mobile field robot that is used in a field having sub-regions.

With the foregoing overview of the autonomous field robot system 100 and the various components of the FR 200 and FR 300, it may be helpful now to consider high-level discussions of an example call flow process. To that end, FIG. 4 presents an illustrative process 400 for an autonomous mobile field robot that is used in a field having sub-regions. The process 400 is illustrated as a logical flow, which represents a sequence of operations that can be implemented in hardware, software, or a combination thereof. In the context of software, the blocks represent computer-executable instructions that, when executed by one or more processors, perform the recited operations. Generally, computer-executable instructions may include routines, programs, objects, components, data structures, and the like that perform particular functions or implement particular abstract data types. The order in which the operations are described is not intended to be construed as a limitation, and any number of the described blocks can be combined in any order and/or in parallel to implement the process. For discussion purposes, the process 400 of FIG. 4 is described with reference to the architecture of the system 100 of FIG. 1 and the FR of FIG. 2.

In step 402, a determination of the map of the field is made. In various embodiments, the FR 200 may be preprogrammed to include a map of the field. Alternatively, the FR 200 may determine the map of the field 104 by performing a preliminary sweep of the field 104. In one embodiment, the FR 200 may divide the field into sub-regions 106 based on an estimated time it would take for the FR 200 to administer (e.g., perform soil mechanics, determine temperature, irrigate, adjust one or more parameters of the soil of the sub-region, etc.) For example, sub-regions may be divided based on estimated time segments, such as 2 hours, 24 hours, etc., depending on the particular type of field and application.

In step 404, a path of the FR 200 to traverse the field 104 is identified. In various embodiments, the goal of an FR 200 may be to administer (e.g., care) for one sub-region, several sub-regions, or all sub-regions of a field 104. To that end, a traveling salesperson algorithm may be used to determine the shortest distance or time from the starting location to various sub-regions. Alternatively, a greedy algorithm, where the nearest neighbor is navigated to after visiting a node, may be used to navigate the field. In one embodiment, various sensors, such as, radar, infrared, laser, and cameras are used to make sure that the FR 200 does not interfere with an impediment. The impediments may be stored in a memory of the FR 200 and later transferred to the monitoring server 130 for machine learning purposes. For example, if an FR 200 senses an obstacle, such as a ditch, tree, boulder, etc., it may use its artificial intelligence to navigate around it. Its learned route may be stored and used by the same (or another FR) at a more efficient pace (without having to slow down to learn about obstacles).

In step 406, soil mechanics are performed of each sub-region using the environmental sensors. The soil mechanics include at least one of the following for each sub-region of the field 104: nutrient composition (e.g., major nutrients, secondary nutrients, and minor nutrients), chemical composition, permeability, acidity, pH level, contaminant level, water content, specific gravity, liquid limit, and plastic limit. In one embodiment, the environmental sensors of the FR 200 can perform air quality analysis, including the following parameters of air: chemical composition & contaminants, biological composition & contaminants, an air quality index, etc. The environmental sensors may also detect the presence of pests via the imaging device, to recognize plant damage from such pests.

The environmental sensors that are used to make the above measurements may include, but are not limited to, a temperature sensor, a humidity sensor, an imaging device, a nutrient sensor, a chemical composition sensor, an acidity sensor, a pH sensor, a contaminant level sensor, a water content sensor, a specific gravity sensor, a liquid limit sensor, and a plastic limit sensor.

In step 408, the soil of the temperature is determined for each sub-region. The soil mechanics together with the soil temperature are referred to herein as the soil metrics. In various embodiments, the FR 200 measures the surface of the soil and also a predetermined distance below the soil by inserting a thermometer into the soil. The temperature measurement may be provided in open areas and in areas that have shade (whether natural or artificial via the robot). In one embodiment, whether to perform a temperature measurement is indicated by a camera (e.g., imaging device). The surface temperature may be measured with a laser thermometer. To measure the temperature of the soil at a predetermined distance, a small hole may be introduced by the FR 200 into the soil, such that the laser thermometer can perform an accurate temperature measurement. In one embodiment, air temperature of the sub-region is measured as well.

While the determination of the soil metrics and temperature have been illustrated as separate steps for each sub-region, in various embodiments they may be (i) performed at the same time or (ii) in sequence while the FR 200 is at each sub-region, respectively. Put differently, in one embodiment, all the soil metrics may be performed when an FR 200 is at a sub-region. In another embodiment, the soil metrics may be performed at different times or by different FR's that are specialized to perform such metrics, respectively.

In step 410, data is sent to the monitoring server 130. The data may include the soil metrics, the time the measurements were performed, the GPS location within the sub-region, and other identification information. The FR 200 may send the data (including the soil metrics) over the RAN 122. In turn, the monitoring server 130 may store the data in the data store 150. For example, if the FR 200 is one of a plurality of robots used on the field 104, each FR 200 may provide identification information to the monitoring server, such that the source of the data can be discerned.

In one embodiment, an FR 200 can receive data from the monitoring server 130 or any other source, such as the internet 128, or a weather station, to determine the weather forecast for each sub-region.

In step 412, the FR 200 determines whether to irrigate a sub-region of a field 104. In various configurations, the FR 200 has the ability to irrigate the soil that is beneath its path (e.g., beneath its central horizontal axle). Whether to irrigate and the amount of irrigation to perform is based on the soil metrics and the weather forecast. For example, the rate and depth of irrigation for each sub-region may be based on the soil mechanics, the soil temperature, and the estimated precipitation expected from the weather forecast for each sub-region, respectively. If FR 200 determines that further irrigation is beneficial, the method continues with step 414, where the sub-region of the field is irrigated.

In step 416, the FR 200 determines whether to adjust one or more parameters of each sub-region. This determination, as well as the amount and type of chemicals, are based on the soil metrics. If FR 200 determines that an adjustment of one or more parameters is warranted, the method continues with step 418, where the one or more chemicals are released from the FR 200, as appropriate.

In step 420, the FR 200 determines whether to provide shade to a sub-region. This determination, as well as the length of time shade is to be provided, are based on the soil metrics. If FR 200 determines that shade is warranted for a sub-region, the method continues with step 422, where shade is provided to the subject sub-region.

In step 424, the FR 200 determines whether artificial UV light should be provided to a sub-region. This determination, as well as the length of time artificial light is to be provided, are based on the soil metrics. If FR 200 determines that additional light is warranted for a sub-region, the method continues with step 426, where shade is provided to the subject sub-region.

It should be noted that, in various embodiments, steps 412 to 424 below) can be performed after a primary sweep of several sub-regions of the field 104 by an FR 200 to determine the soil metrics, or immediately after the soil metrics have been determined for each sub-region. For example, the soil metrics of all the sub-regions may be performed first, and then, the FR 200 (or one or more other FR's) may return to each sub-region to provide irrigation, adjustment of parameters, etc. Thus, the care for a sub-region may be performed (i) after an analysis phase of all the sub-regions, or (ii) concurrently (e.g., immediately) after (or during) an analysis of the subject sub-region.

In step 430, the FR 200 returns to the home station. While flow 400 illustrates the return to the home station 430 to be performed at the end of the flow 400, in one embodiment, the FR 200 constantly monitors the water, chemicals, fuel, etc., and returns to the home station for replenishment of the depleted resource(s) when predetermined thresholds are met. In one embodiment, an administrator of the FR 200 and/or field manager is notified when resources are to be replenished. To that end, the notification may be sent via the RAN 122 of FIG. 1 to the appropriate recipient. The notification may include the resource to be replenished (e.g., water, chemicals, materials, etc.). The chemicals may include fertilizer, pesticide, and the like. Upon replenishment, the FR 200 may send another notification to the appropriate recipient indicating that the replenishment is complete and that the FR 200 is resuming its autonomous operations on the field 104.

Additional Considerations and Embodiments

In various embodiments, the field robot discussed herein is capable of various smart behaviors. In one example, the FR performs behavior-based robotics, such as learning from the data stored in the data store 150. To that end, an FR may include artificial intelligence that is programmed into the memory of an FR. Smart behaviors include automated planning & control, interaction with other FR's on the field to perform swarm robotics, machine learning; group-based robotics, and swarm intelligence. Accordingly, each FR is able to exhibit complex behaviors based on the feedback FR receives from its immediate environment, other FR's and the monitoring server 130, gradually correcting its actions. As its actions are optimized, the learned behavior may be sent to other FR's via wireless communication. The learned behavior may be sent directly to other FR's or indirectly by first sending relevant data to a monitoring server 130, which in turn routes the learned behavior to other FR's, such that the FR's can work in concert as a team on the field 104 and benefit from the knowledge obtained from each team FR.

Accordingly, the FR has the ability to communicate with other FR's as well as one or more home stations to initiate an action as a single field unit/robot or as a group using group-based (i.e., two or more robots/field units) approaches. Such communication might include group-based decision-making and actions based on consensual analysis/decision-making. Behaviors might include synthetic-motivational behaviors (such as seeking goals, flocking, dispersion/aggregation, follow-the-leader, or collision-avoidance) to automate the navigation/locomotion/direction of a group of field units/robots; procedural behaviors based on programmed step-by-step conditions/responses; or group behaviors based on reactive decision-making from real-time data inputs, among others.

An example of two FR's coordinating coverage of a field is to first subdivide a field into two equal size sub-regions. A first FR may scan the first sub-region and a second FR may scan the other sub-region. After scanning the sub-regions with their sensors, the two FR's may share information about the scans to determine the tasks to perform in maintaining the field. The sharing may be done either by sending the sensor scan data to a central server (e.g., monitoring server 130) to analyze the data, or may be done on a peer to peer basis by the robots. Once the tasks are identified, the tasks are separated into two queues of work based on priority, estimated amount of time to perform, and proximity of tasks. In this way two queues of work are created. The first queue is dispatched to the first FR and the second queue is dispatched to the second FR. The two FR's then perform their tasks as described with respect to FIG. 4.

As discussed above, each FR may be equipped with multiple sensors/monitors that may allow the FR to monitor various components and parts of the field unit/robot, total/used weight/amounts of any on boarded materials (e.g., water, fertilizer, pesticide) as well as usage/uptime/life metrics of different parts of entire unit. Such metrics may include (but are not limited to): total number of hours of operation; (2) total number of hours of being stationary; (3) total number of hours of moving; (4) number of gallons/liters water carried and/or dispensed for each sub-region; (5) an average amount of water moved during a predetermined time period; (6) an average weight of the load carried; (7) a total number of engine hours; (8) total number of hours on the solar panels attached to the wings; (9) a solar conversion rate for solar panels, etc.; (10) and additional sensors that do self-monitoring (determining the health of the FR itself).

Example Computer Platform

As discussed above, functions relating to autonomously administering a field can be performed on one or more computers connected for data communication via the components of a radio access network 122, including FR 102(1) to 102(n), monitoring server 130, and data store 150, as shown in FIG. 1 and in accordance with the call flow of FIG. 4. Although special purpose devices may be used as the server(s), such as servers 130 and 150 in FIG. 1, such devices also may be implemented using one or more hardware platforms intended to represent a general class of data processing device commonly used to run "server" programming so as to implement the functions discussed above, albeit with an appropriate network connection for data communication.

Figure 5:
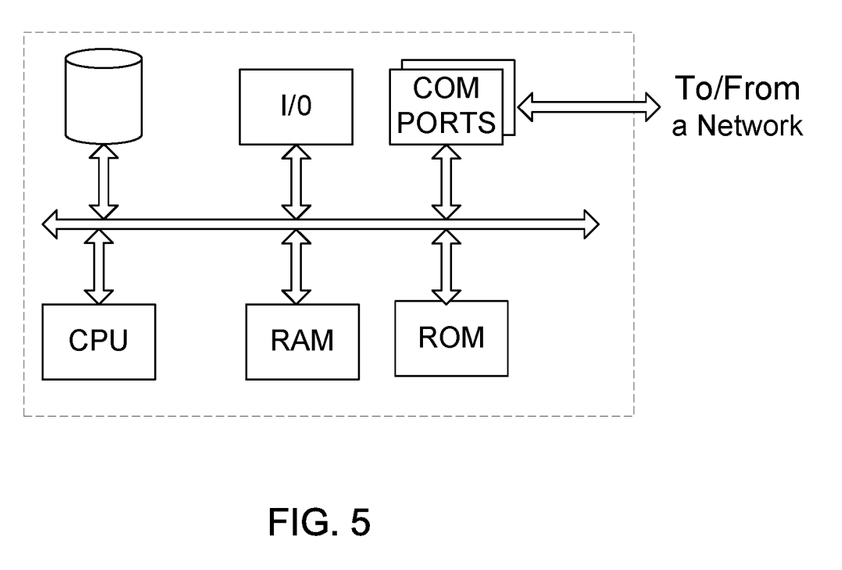
FIG. 5 provides a functional block diagram of a general purpose computer hardware platform that may be used to implement one or more servers of FIG. 1.

FIG. 5 provides a functional block diagram of a general purpose computer hardware platform. FIG. 5 illustrates a network or host computer platform, as may typically be used to implement a server, such as the monitoring server 130 or data store 150. It is believed that the general structure and general operation of such equipment as shown in FIG. 5 should be self-explanatory from the high-level illustrations.

A general purpose computer configured as a server, for example, includes a data communication interface for packet data communication. The server computer also includes a central processing unit (CPU), in the form of one or more processors, for executing program instructions. The server platform typically includes an internal communication bus, program storage and data storage for various data files to be processed and/or communicated by the server, although the server often receives programming and data via network communications. The hardware elements, operating systems and programming languages of such servers are conventional in nature. Of course, the server functions may be implemented on a cloud and/or in a distributed fashion on a number of similar platforms, to distribute the processing load. As discussed above, in various other embodiments, the functionality of the monitoring server 130 and data store 150 may be combined in one or more server platforms. In one embodiment, the monitoring server 130 in combination with the data store 150 represents a platform that allows the processing of big data, which may be over a cloud.

CONCLUSION

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

It is understood that any specific order or hierarchy of steps in the processes disclosed in FIG. 4 are illustrations of exemplary approaches. Based upon design preferences, it is understood that the specific order or hierarchy of steps in the processes may be rearranged, expanded, and some steps omitted. Some of the blocks may be performed simultaneously.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

What is claimed is:

1. An autonomous mobile field robot configured to be used in a field having sub-regions, the field robot comprising:
   one or more environment sensors;
   a global positioning system (GPS) receiver;
   one or more collapsible set of wings having a first position to let light through to at least one of the sub-regions and a second position to block the light and to provide shade to the at least one sub-region;
   one or more chemical storage units for adjusting one or more parameters of a soil of the sub-regions;
   a processor;
   a network interface coupled to the processor configured to enable communications via a radio access network;
   a storage device for content and programming;
   a program stored in the storage device, wherein execution of the program by the processor configures the field robot to perform acts comprising:
      performing soil mechanics with the one or more environment sensors at each sub-region and storing the soil mechanics in the storage device;
      determining a soil temperature of each sub-region and storing the soil temperature in the storage device;
      sending the soil mechanics and the soil temperature for each sub-region to a monitoring server via the radio access network for storage and analysis;
      adjusting one or more parameters of the soil of a sub-region based on the soil mechanics of the corresponding sub-region with the chemicals from the one or more chemical storage units;
      determining whether to provide shade to the sub-region based on at least one of the soil mechanics and the soil temperature corresponding to the sub-region; and
      setting the one or more collapsible set of wings to the second position to provide the shade to the sub-region in response to determining to provide the shade.

2. The field robot of claim 1, further comprising a water storage device configured to irrigate the one or more sub-regions.

3. The field robot of claim 2, wherein execution of the program further configures the field robot to perform acts comprising:
   irrigating each sub-region of the field by releasing water carried on the field robot, based on the soil mechanics and the soil temperature of each sub-region, respectively.

4. The field robot of claim 1, further comprising one or more light sources configured to provide UV light to a sub-region of the field.

5. The field robot of claim 1, wherein the soil mechanics include at least one of the following for each sub-region of the field:
   (i) a nutrient composition,
   (ii) a chemical composition,
   (iii) an acidity,
   (iv) a pH level,
   (v) a contaminant level,
   (vi) a water content,
   (vii) a specific gravity,
   (viii) a liquid limit, and
   (ix) a plastic limit.

6. The field robot of claim 1, wherein the environment sensors include at least one of: a temperature sensor, a humidity sensor, an imaging device, a nutrient sensor, a chemical composition sensor, an acidity sensor, a pH sensor, a contaminant level sensor, a water content sensor, a specific gravity sensor, a liquid limit sensor, and a plastic limit sensor.

7. The field robot of claim 3, wherein execution of the program further configures the field robot to perform acts comprising:
   receiving a weather forecast over the radio access network; and
   adjusting the irrigation of a sub-region based on the soil mechanics, a soil temperature, and an estimated precipitation expected from the weather forecast for the respective sub-region.

8. The field robot of claim 7, wherein a rate and depth of irrigation for each sub-region is based on the soil mechanics, the soil temperature, and the estimated precipitation expected from the weather forecasts for the respective sub-region.

9. The field robot of claim 1, wherein a first side of each wing includes a solar panel configured to charge the field robot.

10. The field robot of claim 9, wherein a second side of at least one wing includes one or more light sources configured to provide UV light to a sub-region of the field.

11. The field robot of claim 1, wherein the chemical storage units include at least one of: (i) a fertilizer unit, and (ii) a pesticide unit.

12. The field robot of claim 1, wherein execution of the program further configures the field robot to perform acts comprising: receiving, wirelessly, location coordinates of a sub-region to be serviced by the field robot from one or more other field robots.

13. The field robot of claim 1, wherein execution of the program further configures the field robot to perform acts comprising: receiving location coordinates of a sub-region to be serviced by the field robot from the monitoring server.

14. The field robot of claim 1, wherein execution of the program further configures the field robot to perform acts comprising: sending a data packet comprising the soil mechanics, the soil temperature, and GPS coordinates of a sub-region to one or more other field robots for servicing the sub-region.

15. An agricultural automation system comprising:
a plurality of wirelessly interconnected field robots;
a home station configured to refill at least one of (i) water and (ii) chemicals of at least some of the plurality of field robots;
a remote monitoring server that is wirelessly interconnected to the field robots; wherein:
a first field robot of the plurality of field robots is configured to:
perform soil mechanics with one or more of its environmental sensors on each sub-region of a field;
determine a soil temperature of each sub-region; and
send the soil mechanics and soil temperature of each sub-region to the monitoring server over a radio access network;
a second field robot of the plurality of field robots is configured to:
receive instructions from the monitoring server based on the soil mechanics and the soil temperature of a sub-region of the agricultural from the first field robot;
irrigate the sub-region of the field by releasing water carried on the second field robot, based on the received instructions from the monitoring server;
expand one or more collapsible set of wings of the second field robot at the sub-region based on the instructions from the monitoring server;
adjust one or more parameters of the soil of the sub-region based on the instructions from the monitoring server; and
return to the home station to refill at least one of (i) the water, and (ii) the chemicals of the second field robot; and
the monitoring server is configured to:
determine whether to provide shade to the sub-region based on at least one of the soil mechanics and the soil temperature corresponding to the sub-region; and
send the instructions to the second field robot to expand the one or more collapsible set of wings in response to determining to provide the shade.

16. A method of operating a field robot having one or more environmental sensors and one or more chemical storage units, the method comprising:
performing soil mechanics with the one or more environment sensors on each sub-region;
determining a soil temperature of each sub-region;
sending the soil mechanics and the soil temperature for each sub-region to a monitoring server via a radio access network for storage and analysis;
irrigating each sub-region of the field by releasing water carried on the field robot, based on the soil mechanics and the soil temperature of each sub-region, respectively;
adjusting one or more parameters of the soil of a sub-region based on the soil mechanics of the corresponding sub-region with chemicals from one or more chemical storage units of the field robot;
determining whether to provide shade to the sub-region based on the soil mechanics and soil temperature corresponding to the sub-region;
changing a position of one or more collapsible set of wings included on the field robot from a vertical position that lets light to the sub-region to a horizontal position that blocks the light to provide shade to the sub-region, wherein the changing of the position is in response to determining to provide the shade to the sub-region; and
returning to a home station to refill at least one of (i) the water and (ii) the chemicals.

17. The field robot of claim 1, wherein the first position of the one or more collapsible set of wings includes a vertical position to let the light through to the at least one sub-region, and the second position includes a horizontal position to block the light.

18. The field robot of claim 1, wherein the one or more collapsible set of wings are detachable from the field robot, and wherein execution of the program further configures the field robot to perform acts comprising:
determining whether to deploy the one or more collapsible set of wings to the sub-region; and
detaching the one or more collapsible set of wings in response to determining to deploy the one or more collapsible set of wings.

19. The field robot of claim 18, wherein execution of the program further configures the field robot to perform acts comprising:
storing, to the storage device, a location of the one or more collapsible set of wings in response to deploying the one or more collapsible set of wings.

20. The field robot of claim 19, wherein execution of the program further configures the field robot to perform acts comprising:
determining to retrieve the one or more collapsible set of wings, wherein determining to retrieve the one or more collapsible set of wings comprises at least one of:
returning to the location based on position information obtained via the GPS receiver to retrieve the one or more collapsible set of wings; or
instructing another field robot to retrieve the one or more collapsible set of wings.

* * * * *